(12) United States Patent
Sturgis et al.

(10) Patent No.: US 10,555,884 B2
(45) Date of Patent: Feb. 11, 2020

(54) 2-PYRIDINOL-N-OXIDE DEODORANT AND ANTIPERSPIRANT COMPOSITIONS

(71) Applicant: The Procter & Gamble Company, Cincinnati, OH (US)

(72) Inventors: David Arthur Sturgis, Montgomery, OH (US); Stevan David Jones, Hyde Park, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 16/021,877

(22) Filed: Jun. 28, 2018

(65) Prior Publication Data

US 2019/0000736 A1    Jan. 3, 2019

Related U.S. Application Data

(60) Provisional application No. 62/527,180, filed on Jun. 30, 2017.

(51) Int. Cl.
| | | |
|---|---|---|
| *A61K 8/49* | (2006.01) | |
| *A61K 8/41* | (2006.01) | |
| (Continued) | | |

(52) U.S. Cl.
CPC .......... *A61K 8/4926* (2013.01); *A61K 8/0229* (2013.01); *A61K 8/0241* (2013.01); *A61K 8/19* (2013.01); *A61K 8/33* (2013.01); *A61K 8/347* (2013.01); *A61K 8/368* (2013.01); *A61K 8/41* (2013.01); *A61K 8/413* (2013.01); *A61K 8/42* (2013.01); *A61K 8/44* (2013.01); *A61K 8/55* (2013.01); *A61K 8/675* (2013.01); *A61K 8/8129* (2013.01); *A61K 8/922* (2013.01); *A61K 8/965* (2013.01); *A61Q 15/00* (2013.01); *A61K 2800/30* (2013.01); *A61K 2800/31* (2013.01);
(Continued)

(58) Field of Classification Search
CPC .. A61K 8/4926; A61K 8/0229; A61K 8/0241; A61Q 15/00
See application file for complete search history.

(56) References Cited

U.S. PATENT DOCUMENTS

| | | |
|---|---|---|
| 3,792,068 A | 2/1974 | Luedders et al. |
| 3,887,692 A | 6/1975 | Gilman |
| (Continued) | | |

FOREIGN PATENT DOCUMENTS

| | | |
|---|---|---|
| BE | 825146 A1 | 8/1975 |
| GB | 2048229 | 12/1980 |
| (Continued) | | |

OTHER PUBLICATIONS

Kontoghiorghes et al, "2-Hydroxypyridine-N-Oxides: Effective New Chelators in Iron Mobilisation", Biochim Biophys ACta, 924(1)13-8 (Year: 1987).*

(Continued)

*Primary Examiner* — Carlos A Azpuru
(74) *Attorney, Agent, or Firm* — Kathleen Y. Carter

(57) ABSTRACT

A deodorant stick having a substituted or unsubstituted 2-pyridinol-N-oxide material and at least one material selected from the group consisting of hexamidine, magnesium carbonate, zinc carbonate, thymol, magnesium hydroxide, dead sea salt, calcium carbonate, polyvinyl formate, salycilic acid, niacinamide, and combinations thereof.

15 Claims, 2 Drawing Sheets

(51) Int. Cl.

| | |
|---|---|
| *A61K 8/42* | (2006.01) |
| *A61K 8/55* | (2006.01) |
| *A61K 8/34* | (2006.01) |
| *A61K 8/19* | (2006.01) |
| *A61K 8/67* | (2006.01) |
| *A61K 8/368* | (2006.01) |
| *A61K 8/33* | (2006.01) |
| *A61K 8/96* | (2006.01) |
| *A61K 8/81* | (2006.01) |
| *A61K 8/02* | (2006.01) |
| *A61K 8/44* | (2006.01) |
| *A61K 8/92* | (2006.01) |
| *A61Q 15/00* | (2006.01) |

(52) U.S. Cl.
CPC .... *A61K 2800/412* (2013.01); *A61K 2800/51* (2013.01); *A61K 2800/74* (2013.01)

(56) References Cited

U.S. PATENT DOCUMENTS

| | | |
|---|---|---|
| 3,904,741 A | 9/1975 | Jones et al. |
| 4,049,792 A | 9/1977 | Elsnau |
| 4,120,948 A | 10/1978 | Shelton |
| 4,359,456 A | 11/1982 | Gosling et al. |
| 4,906,454 A | 3/1990 | Melanson, Jr. |
| 5,019,375 A | 5/1991 | Tanner et al. |
| 5,298,640 A | 3/1994 | Callaghan et al. |
| 5,429,816 A | 7/1995 | Hofrichter et al. |
| 5,675,013 A | 10/1997 | Hani et al. |
| 5,891,424 A | 4/1999 | Bretzler et al. |
| 5,976,514 A | 11/1999 | Guskey et al. |
| 6,624,126 B1 | 9/2003 | Kasuga et al. |
| 2001/0046479 A1 | 11/2001 | Landa |
| 2007/0003499 A1 | 1/2007 | Shen et al. |
| 2013/0045907 A1 | 2/2013 | Lanzalaco |
| 2013/0045910 A1* | 2/2013 | Miracle ................. C11D 3/046 510/276 |
| 2014/0154189 A1 | 6/2014 | Polson et al. |
| 2015/0196477 A1 | 7/2015 | Stark |
| 2016/0326091 A1 | 11/2016 | Rudolph |
| 2017/0172873 A1 | 6/2017 | Banowski |
| 2019/0276389 A1 | 9/2019 | Wos |

FOREIGN PATENT DOCUMENTS

| | | |
|---|---|---|
| GB | 1347950 | 3/1985 |
| WO | WO2004089092 A1 | 10/2004 |
| WO | 2014139449 A1 * | 9/2014 |

OTHER PUBLICATIONS

International Search Report; International Application No. PCT/US2018/039972; dated Mar. 25, 2019; 10 pages.

* cited by examiner

2-PYRIDINOL-N-OXIDE DEODORANT AND ANTIPERSPIRANT COMPOSITIONS

CROSS REFERENCE TO RELATED APPLICATION

This application claims the benefit of U.S. Provisional Application No. 62/527,180, filed Jun. 30, 2017, the substance of which is incorporated herein by reference.

FIELD OF THE INVENTION

The present disclosure relates to deodorant and antiperspirant compositions and methods relating thereto.

BACKGROUND OF THE INVENTION

Many antiperspirant and deodorants use actives that are astringent metallic salts, or in particular, aluminum salts. While aluminum is highly effective as an active, there is consumer interest in antiperspirants and deodorants that do not contain aluminum.

Piroctone olamine is an anti-dandruff active used in shampoos, conditioners, and other treatments. Piroctone olamine can be an effective antimicrobial, but used alone as an active, it may not deliver the hoped for consumer performance. The inventors of the present invention have found, surprisingly, that the combination of piroctone olamine and other antimicrobials can provide significant antimicrobial activity against two of the most common underarm odor bacteria *C. mucofaciens* and *S. epidermidis*, which results in consumer odor protection on par or greater than some of the commonly used commercial deodorants available today.

Also to consider is that impurities can reduce the efficacy of piroctone olamine. Therefore, there is a need to develop products that mitigate this phenomenon and provide higher efficacy. The inventors of the present invention have found that select combinations of chelators and piroctone olamine, such as in an anhydrous formulation or in particular ratios, can provide significantly higher levels of anti-fungal activity than either material alone.

Furthermore, while antimicrobials in antiperspirants and deodorants are known to be able to reduce the microbes on the skin, microbes within hair follicles may still remain and contribute to malodor. The inventors of the present invention have found that piroctone olamine and other antimicrobial powders, if used at a size that can fit into a hair follicle, can deliver surprisingly superior antimicrobial activity.

By utilizing piroctone olamine in combination with appropriate antimicrobials, chelators, and/or at particular particle sizes, the present invention delivers compositions and products with superior antimicrobial performance.

SUMMARY OF THE INVENTION

A cosmetic deodorant stick comprising a substituted or unsubstituted 2-pyridinol-N-oxide material and at least one material selected from the group consisting of hexamidine, magnesium carbonate, zinc carbonate, thymol, magnesium hydroxide, dead sea salt, calcium carbonate, polyvinyl formate, salycilic acid, niacinamide, and combinations thereof.

DETAILED DESCRIPTION OF THE INVENTION

Figure 1:
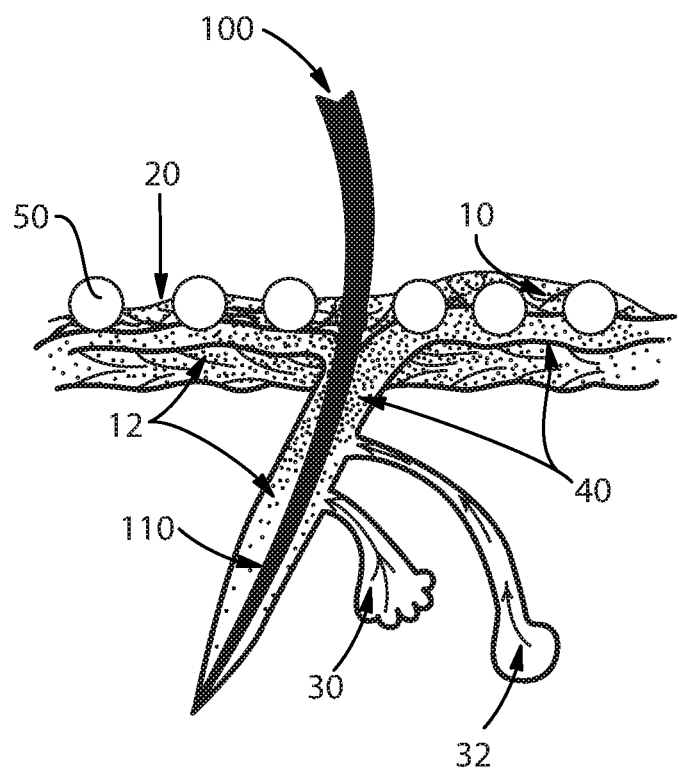
FIG. 1 is an illustration of a hair and hair follicle along with larger antimicrobial particles.

While the specification concludes with claims that particularly point out and distinctly claim the invention, it is believed the present invention will be better understood from the following description.

The present invention can comprise, consist of, or consist essentially of the essential elements and limitations of the invention described herein, as well any of the additional or optional ingredients, components, or limitations described herein.

All percentages, parts and ratios are based upon the total weight of the compositions of the present invention, unless otherwise specified. All such weights as they pertain to listed ingredients are based on the active level and, therefore do not include carriers or by-products that may be included in commercially available materials.

The components and/or steps, including those which may optionally be added, of the various embodiments of the present invention, are described in detail below.

All documents cited are, in relevant part, incorporated herein by reference; the citation of any document is not to be construed as an admission that it is prior art with respect to the present invention.

All ratios are weight ratios unless specifically stated otherwise.

All temperatures are in degrees Celsius, unless specifically stated otherwise.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "effective" means an amount of a subject active high enough to provide a significant positive modification of the condition to be treated. An effective amount of the subject active will vary with the particular condition being treated, the severity of the condition, the duration of the treatment, the nature of concurrent treatment, and like factors.

The term "anhydrous" as used herein means substantially free of added or free water. From a formulation standpoint, this means that the anhydrous antiperspirant and deodorant stick compositions of the present invention contain less than about 1%, and more specifically zero percent, by weight of free or added water, other than the water of hydration typically associated with the particulate antiperspirant active prior to formulation.

The term "ambient conditions" as used herein refers to surrounding conditions under about one atmosphere of pressure, at about 50% relative humidity, and at about 25° C., unless otherwise specified. All values, amounts, and measurements described herein are obtained under ambient conditions unless otherwise specified.

The term "majority" refers to greater than about 51% of the stated component or parameter.

The term "polarity" as used herein is defined by the Hansen Solubility Parameter for solubility.

"Substantially free of" refers to about 2% or less, about 1% or less, or about 0.1% or less of a stated ingredient. "Free of" refers to no detectable amount of the stated ingredient or thing.

The term "volatile" as used herein refers to those materials that have a measurable vapor pressure at 25° C. Such vapor pressures typically range from about 0.01 millimeters of Mercury (mm Hg) to about 6 mmHg, more typically from about 0.02 mmHg to about 1.5 mmHg; and have an average boiling point at one (1) atmosphere of pressure of less than about 250° C., more typically less than about 235° C. Conversely, the term "non-volatile" refers to those materials that are not "volatile" as defined herein.

A. 2-Pyridinol-N-Oxide Materials

2-Pyridinol-N-oxide materials suitable for use in this invention include a substituted or unsubstituted 2-pyridinol-N-oxide material or a salt thereof. Included within the scope of this invention are tautomers of this material, e.g., 1-hydroxy-2(1H)-pyridinone. The substituted or unsubstituted 2-pyridinol-N-oxide material and its corresponding tautomeric form, 1-hydroxy-2(1H)-pyridinone, are shown below:

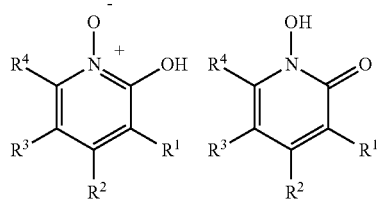

where $R^1$, $R^2$, $R^3$, $R^4$ groups are independently selected from the group consisting of H, Cl, Br, I, F, NO, $NO_2$, and $(CH_2)_nG$, where each G is independently selected from the group consisting of $(O)_mSO_3M^3$, $(O)_mCO_2M^3$, $(O)_mC(O)(R^5)$, $(O)_mC(O)N(R^5R^6)$, $(O)_mCN$, $(O)_m(R^5)$, and $N(R^5R^6)$, where m is 0 or 1, n is an integer from 0 to 4, $R^5$ and $R^6$ are independently selected from the group consisting of H and a substituted or unsubstituted $C_1$-$C_{12}$ organic group, and $M^3$ is selected from the group consisting of H, a substituted or unsubstituted $C_1$-$C_{12}$ organic group, $+N(R^7R^8R^9R^{10})$, and $1/q\ M'^{q+}$ where M' is selected from the group consisting of an alkali metal of charge q and an alkaline earth metal of charge q, where R7, R8, R9, and R10 are independently selected from the group consisting of H and a substituted or unsubstituted $C_1$-$C_{12}$ organic group, and where any pair of vicinal groups, $R^1$ and $R^2$, $R^2$ and $R^3$, $R^3$ and $R^4$ may be taken together to form another five- or six-membered aromatic or aliphatic ring optionally substituted with one or more groups selected from the group consisting of Cl, Br, I, F, NO, $NO_2$, CN, $(CH_2)_nG$, and mixtures thereof. Suitable organic groups include $(C_1$-$C_{12})$alkyl, $(C_2$-$C_{12})$alkenyl, and $(C_2$-$C_{12})$alkynyl. The organic group may optionally be substituted and suitable substituent groups include a hydroxyl group, a carboxyl group, and an amino group. 2-pyridinol-N-oxide is also known, for example, as 2-hydroxypyridine-N-oxide, 2-pyridinol-1-oxide, or 2-hydroxypyridine-1-oxide.

In certain aspects, the 2-pyridinol-N-oxide material is a 2-pyridinol-N-oxide material or tautomer thereof according to the formula(s) above, where $R^1$, $R^2$, $R^3$, $R^4$ are independently selected from the group consisting of H, Cl, and $(CH_2)_nG$, where G is independently selected from the group consisting of $(O)_mSO_3M^3$, $(O)_mCO_2M^3$, $(O)_mC(O)(R^5)$, $(O)_mCN$, and $(O)_m(R^5)$, where m is 0 or 1. In other aspects, the 2-pyridinol-N-oxide material is a 2-pyridinol-N-oxide material according to the formula above, where $R^1$, $R^2$, $R^3$, $R^4$ are independently selected from the group consisting of H, $SO_3M^3$, and $CO_2M^3$. In still other aspects, $R^1$, $R^2$, $R^3$, $R^4$ are independently selected from the group consisting of H, $SO_3M^3$, and $CO_2M^3$, where no more than one $R^1$, $R^2$, $R^3$, $R^4$ is $SO_3M^3$ or $CO_2M^3$.

In certain aspects, the 2-pyridinol-N-oxide material is the salt of a substituted or unsubstituted 2-pyridinol-N-oxide material. In these aspects, the hydrogen of the hydroxyl group of the 2-pyridinol-N-oxide material may be substituted with a suitable charge-balancing cation. In these aspects, non-limiting examples of the hydrogen-substituting cation include $Na^+$, $Li^+$, $K^+$, $1/2\ Mg^{2+}$, or $2\ Ca^{2+}$, substituted ammonium, such as $C_1$-$C_6$ alkanolammnonium, monoethanolamine (MEA), tri-ethanolamine (TEA), di-ethanolamine (DEA), or any mixture thereof. In some aspects, in solution, the cation may be dissociated from the 2-pyridinol-N-oxide or the 1-hydroxy-2(1H)-pyridinone anion.

In certain aspects, the 2-pyridinol-N-oxide material is of a substituted or unsubstituted 2-pyridinol-N-oxide material. Salts for use herein include those formed from the polyvalent metals barium, bismuth, strontium, copper, zinc, cadmium, zirconium and mixtures thereof.

In some aspects, the 2-pyridinol-N-oxide material is selected from the group consisting of: 6-hydroxy-3-pyridinesulfonic acid, 1-oxide (CAS 191672-18-1); 2-hydroxypyridine-1-oxide (CAS 13161-30-3); 2-hydroxy-4-pyridinecarboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridinecarboxylic acid, 1-oxide (CAS 90037-89-1); 2-methoxy-4-quinolinecarbonitrile, 1-oxide (CAS 379722-76-6); 2-pyridinecarboxylic acid, 6-hydroxy-, 1-oxide (CAS 1094194-45-2); 3-pyridinecarboxylic acid, 2-hydroxy-, 1-oxide (CAS 408538-43-2); 2-pyridinol, 3-nitro-, 1-oxide (CAS 282102-08-3); 3-pyridinepropanenitrile, 2-hydroxy-, 1-oxide (193605-60-6); 3-pyridineethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridinepropanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4,6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3);

2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These materials are commercially available from, for example, Sigma-Aldrich (St. Louis, Mo.) and/or Aces Pharma (Branford, Conn.).

In certain aspects, the 2-pyridinol-N-oxide material is a 2-pyridinol-N-oxide material selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof.

In certain aspects, the 2-pyridinol-N-oxide material is a 1-Hydroxy-2(1H)-pyridinone material selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof. These materials are commercially available from, for example, Sigma-Aldrich (St. Louis, Mo.), Princeton Building Blocks (Monmouth Junction, N.J.), 3B Scientific Corporation (Libertyville, Ill.), SynFine Research (Richmond Hill, ON), Ryan Scientific, Inc. (Mt. Pleasant, S.C.), and/or Aces Pharma (Branford, Conn.).

In certain aspects, the 2-pyridinol-N-oxide material is a 2-pyridinol-N-oxide material or tautomer thereof according to the formula(s) below:

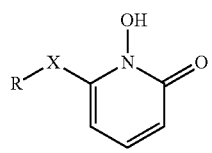

where X is an oxygen or sulfur moiety and R is a substituted or unsubstituted hydrocarbon group having between 1 and 20 carbon atoms. Materials of this class can be synthesized following the procedure disclosed in U.S. Pat. No. 5,675,013.

In certain aspects, the 2-pyridinol-N-oxide material is a 2-pyridinol-N-oxide material or tautomer thereof according to the formula(s) below:

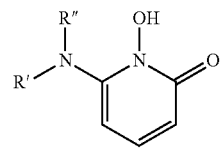

Wherein R' and R" are independently either hydrogen or a substituted or unsubstituted hydrocarbon group having between 1 and 20 carbon atoms. Materials of this class can be synthesized following the procedure disclosed in U.S. Pat. No. 5,675,013. In certain aspects, the 2-pyridinol-N-oxide material is 1-Hydroxy-4-methyl-6-(2,4,4-trimethylpentyl)-2-pyridone monoethanolamine salt.

The amount of 2-pyridinol-N-oxide (which may throughout this disclosure sometimes be referred to as piroctone olamine) in antiperspirant and deodorant formulations of the present invention may be from about 0.1% to about 10% by weight, from about 0.04% to about 1.0% by weight, in some embodiments from about 0.05% to about 0.6% by weight, and in some embodiments from about 0.05% to about 0.5% by weight of the antiperspirant or deodorant stick.

B. Chelators

In the present invention, iron chelators may have, but are not limited to, the following characteristics:

1. An affinity for iron ions in either the ferrous (iron II) or ferric (III) forms;
2. Materials of Description 1 (above) that have a denticity of four or higher (denticity is the number of groups of a molecule that bind to the iron);
3. Chemical descriptions that are a subset of Description 2:
   a. Either natural or synthetic materials;
   b. Materials of the following chemical classes:
      i. Aminophosphates
      ii Aminocarboxylates
      iii. Hydroxamic acids and molecules representing combinations of these chemical classes.

In an embodiment of the present invention, an iron chelator may be present from the following groups:

(1) Iron Chelators Represented by the Following Structure

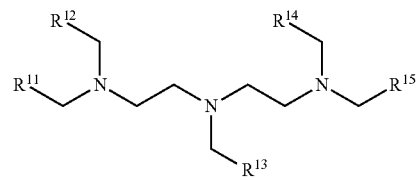

where $R^{11}$, $R^{12}$ $R^{13}$, $R^{14}$, $R^{15}$ are independently selected from the group consisting of $M^1M^2PO_3$, $CO_2M^1$, and mixtures thereof where $M^1$ and $M^2$ is H, a metal salt (such as Na, K, Ca, Mg, Al, etc.) or ammonium salt.

(2) Iron Chelators Represented by the Following Structure

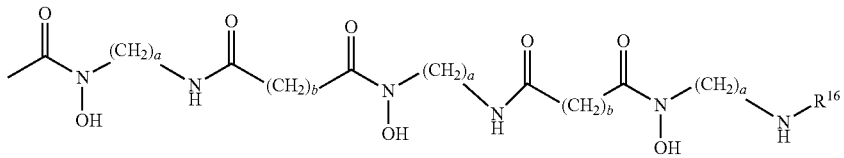

where a is an integer from 2 to 7 wherein any of the CH$_2$ groups in this unit may be substituted with alkyl or aryl units that may contain heteroatoms (S, N, O, Cl, F, Br or I)

where b is an integer from 1 to 7 wherein any of the CH$_2$ groups in this unit may be substituted with alkyl or aryl units that may contain heteroatoms (S, N, O, Cl, F, Br or I)

where R$^{16}$ is H or (CH$_2$)$_n$, where n in an integer from 1 to 6 or is a CH$_2$ linker unit that may be further substituted at any CH$_2$ group in the chain with alkyl or aryl units that may contain heteroatoms (S, N, O, Cl, F, Br, or I).

Specific and/or additional chelators in the present invention may include, but are not limited to, diethylenetriaminepentaacetic acid (DTPA), diethylenetriaminepentakis (methylenephosphonic acid) (DTPMP), desferrioxamine, their salts and combinations thereof, EDTA, DPTA, EDDS, enterobactin, desferrioxamine, HBED, and combinations thereof.

While piroctone olamine can be an effective antimicrobial for antiperspirants or deodorants, the presence of iron and other impurities may reduce piroctone olamine's effectiveness. As such, the inventors of the present invention have found that including a chelant to bond with iron, for example, can reduce the occurrence of piroctone olamine itself bonding with the iron, essentially freeing the piroctone olamine to be effective against bacteria.

This is particularly true in anhydrous formulations. In an aqueous formulation comprising piroctone olamine and a chelant, the chelant can improve piroctone olamine's efficacy because the chelant should have more affinity for the iron than the piroctone olamine has affinity for the iron. In addition, in an anhydrous formulation, with little or no water, the water solubility of the materials comes into play when sweat meets the formulation. Piroctone olamine typically has a lower water solubility than a chelant, meaning that in an anhydrous formulation, the chelant's higher water solubility results in the chelant more quickly getting into solution and bonding with iron, ie., before the piroctone olamine gets into solution. This further advantage only exists in an anhydrous formulation, as in an aqueous formulation, everything is fully in solution from the beginning.

Table 1 below shows the intrinsic water solubility independent of pH (Log WS$_o$) of piroctone olamine and EDTA as an example. The lower Log WS$_o$ of piroctone olamine indicates that it will get into solution more slowly than a chelant such as EDTA, and the chelant will have more of an opportunity to bond with iron than the piroctone olamine will.

TABLE 1

| CAS Number | Name | LogWS$_o$ |
|---|---|---|
| 6153824 | Piroctone olamine | −3.22 |
| 6153825 | EDTA | −1.4 |

Furthermore, the inventors of the present invention have found that the ratio of chelant to piroctone olamine is especially important. In some embodiments, the improved efficacy of a chelant with piroctone olamine can be seen when the ratio of chelant to piroctone is at least about 4:1, in some embodiments at least 6:1, and in some embodiments, at least 8:1.

C. Additional Antimicrobials

In addition to piroctone olamine, the present invention may include other antimicrobial compositions. For example, other antimicrobials may include, without being limited to, hexamidine, magnesium carbonate, zinc carbonate, thymol, magnesium hydroxide, dead sea salt, a combination of magnesium hydroxide and magnesium carbonate, calcium carbonate, sodium carbonate, magnesium carbonate hydroxide, partially carbonated magnesium hydroxide, polyvinyl formate, salycilic acid, niacinamide, phenoxyethanol, eugenol, linolenic acid, dimethyl succinate, citral, triethyl citrate, sepiwhite, cinnamon essential oil, cinnamon bark essential oil, cinnamic aldehyde, and combinations thereof.

Any of the antimicrobials of the present invention may be used as powders. It is believed that antimicrobial powders may provide a better deposition and have more longevity on the skin than antimicrobials delivered in a different form. In addition, it is believed that antimicrobial powders of a certain average particle size, typically from about 1 micron to about 5 microns, may provide a significant increase in antimicrobial efficacy.

Many antimicrobials can be effective at minimizing the skin surface bacteria. However, as a leave-on product where odor may not occur until later, even hours after application, deodorant antimicrobials are needed that will be effective for long periods of time. So while deodorant antimicrobials may be effective immediately upon application on the skin, it is believed that odor comes back quickly because the bacteria living around the hair follicle can quickly repopulate the skin surface bacteria. Historical approaches using high skin penetrating liquid antimicrobials to affect this region (for example, hexanediol) can cause irritation. Therefore, the present invention is able to target methods and mechanisms that can more effectively deliver antimicrobials not only to the skin surface, but to the bacteria in and around the hair follicle. While not wanting to be bound to the theory, the inventors of the present inventor believe that powders, specifically powders with an average particle size of less than about 10 microns, in some cases from about 1 micron to about 5 microns, are more efficient at getting into the hair follicle where the bacteria live and repopulate the skin surface.

Figure 2:
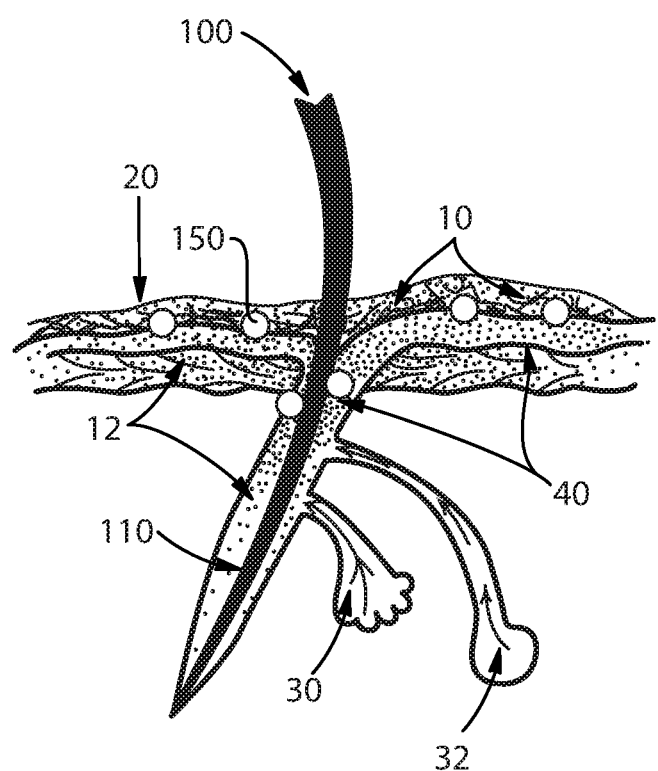
FIG. 2 is an illustration of a hair and hair follicle along with smaller antimicrobial particles.

As shown in FIGS. 1 and 2, a hair 100 is partly above the skin surface and partly below the skin surface in the hair follicle 110. The antimicrobial particles, 50 and 150, upon application, may be on the surface of the skin at the skin secretion/air/sweat interface 20 and where there is bacteria 10. As shown in FIGS. 1 and 2, the sebaceous gland 30 and the apocrine gland 32 in the skin have secretions that are in the hair follicle 110. Bacteria 12 and odor precursors 40 are embedded in the secretions. In FIG. 1, the larger antimicrobial particles 50 are too big to fit into the hair follicle, leaving the secretions inside the hair follicle untouched. The antimicrobial particles 50 come in contact with bacteria only on the surface of the skin. In FIG. 2, however, the antimicrobial particles 50 are sized to fit within the hair follicle and deliver antimicrobial activity not only to the surface of the skin, but also directly and immediately to the hair follicle secretions 12 and 40. Having the antimicrobial particles be in the range of about 1 to about 10 microns, in some embodiments about 1 to about 5 microns, provides better odor protection later in the day hours after application of the deodorant when other good antimicrobial materials and other sizes of antimicrobial materials are not as effective against this rebound in bacteria population from the follicle.

D. Antimicrobial Activity

Table 2 below shows the raw material microbial inhibition concentration data tested against two key underarm bacteria strains. As can be seen, the first three listed antimicrobials, lupamin, hexamidine, and piroctone olamine, perform particularly well against the bacteria as raw materials. Also performing well as raw materials are phenoxyethanol, eugenol, linolenic acid, dimethyl succinate, citral, triethyl citrate, and sepiwhite. Also performing moderately well against the bacteria as raw materials were dead sea salt (magnesium carbonate and magnesium hydroxide) and calcium carbonate.

TABLE 2

| Antimicrobial | C. mucofaciens | S. epidermidis |
| --- | --- | --- |
| Lupamin | <2 ppm | 4 ppm |
| Hexamidine 36 mg/ml H2O | <2 ppm | 7 ppm |
| 100 mg/ml piroctone olamine in H2O | <5 ppm | 10 ppm |
| 100% Phenoxyethanol | 400 ppm | 800 ppm % |
| Eugenol 99% ETOH | 773 ppm | 773 ppm |
| Linolenic Acid 70% ETOH | 1093 ppm | 1093 ppm |
| Dimethyl Succinate 98% ETOH | 1531 ppm | 3062 ppm |
| Citral 96% ETOH | 1500 ppm | 1500 ppm |

TABLE 2-continued

| Antimicrobial | C. mucofaciens | S. epidermidis |
| --- | --- | --- |
| 100% Triethyl citrate | 1600 ppm | 1600 ppm |
| Sepiwhite 40 mg/ml H2O ins | 2000 ppm | 1000 ppm |
| Magnesium Carbonate & Magnesium Hydroxide 50 mg/ml H2O ins | >2500 ppm | >2500 ppm |
| Ca Carbonate 50 mg/ml H2O ins | >2500 ppm | >2500 ppm |
| Linoleic acid 100% ETOH | 3125 ppm | 3125 ppm |
| Conarom B (beta Bio) 100% ETOH | 3125 ppm | 3125 ppm |
| Hexyl Decanol 97% ETOH | 6062 ppm | 3031 ppm |
| Ajowan oil 50% ETOH | 12500 ppm | 6300 ppm |
| Oregano oil 50% ETOH | 12500 ppm | 6300 ppm |
| 100% Ethylhexyl glycerin | 12500 ppm | 12500 ppm |
| Mineral oil 50% in ETOH | 12500 ppm | >50000 ppm |
| ACH 50% in H2O | 25000 ppm | 25000 ppm |
| NaCl 250 mg/ml H2O | >25000 ppm | >25000 ppm |
| Farnesol 95% ETOH | 47500 ppm | 5937 ppm |
| Phytol 97% ETOH | >49000 ppm | >49000 ppm |
| Nerolidol 98% ETOH | >49000 ppm | >49000 ppm |
| CaCl 500 mg/ml H2O | >50000 ppm | >50000 ppm |
| Isopropyl Myristate 98% ETOH | >59000 ppm | >59000 ppm |

While numerous antimicrobials exhibit efficacy against two main bacteria strains that deodorants try to address, due to regulatory and safety reasons, there are sometimes limits as to how much of a particular antimicrobial may be put into an deodorantformula. Therefore, there is a need for multiple antimicrobials to work together in a formula to deliver enough long-term odor protection. The inventors of the present invention believe that piroctone olamine is an ideal antimicrobial to combine with other antimicrobials.

Table 3 is a summary of in-use Consumer Data for Males and Females for Odor Protection. Inventive Formula 1 (shown in the examples in Table 4) includes a combination of several antimicrobials, specifically piroctone olamine combined with hexamidine and dead sea salt. As seen in Table 3, the inventive formula 1 performed better than competitive products in keeping underarms from malodor (Competitive DO #1 is Tom's of Maine, Apricot, Competitive DO #2 is Schmidt's, Bergamot+Lime, and Competitive DO #3 is Lavanila, Vanilla and Lemon.) Consumer data test method: Phase 1 was four days of soap washing only (no underarm product use). Both phase 2 and 3 included once per day application of test products for eight days. The desired dose was 0.9 g. Subjects were asked to complete twice daily self-assessed odor evaluations and once daily discomfort evaluation.

Inventive Formulas 2-5 in Table 4 are additional combinations of piroctone olamine with additional antimicrobials.

TABLE 3

|  | Keeping Underarms from Malodor (% who answered Excellent or Very Good) | Keeping Underarms from Malodor (% who answered Fair or Poor or Very Good) |
|---|---|---|
| Males (n = 36-48) | | |
| Inventive Formula #1 | 80 | 4.4 |
| Competitive DO #1 | 79.2 | 10.4 |
| Competitive DO #2 | 62.8 | 16.3 |
| Competitive DO #3 | 69 | 16.7 |
| Females (n = 64-71) | | |
| Inventive Formula #1 | 78.1 | 9.4 |
| Competitive DO #1 | 63.8 | 23.2 |
| Competitive DO #2 | 87.5 | 6.3 |
| Competitive DO #3 | 53.8 | 21.5 |

TABLE 4

E. Examples

|  | Inventive Formula #1 | Inventive Formula #2 | Inventive Formula #3 | Inventive Formula #4 | Inventive Formula #5 |
|---|---|---|---|---|---|
| Cyclopentasiloxane | 37.3 | 40.3 | 40.25 | | |
| Caprylic/Capric Triglyceride | | | | 67.05 | 52.9 |
| Mineral Oil | 8 | 8 | 8 | | |
| Dimethicone | 10 | 10 | 10 | | |
| PPG-14 butyl ether | 5 | 5 | 5 | | |
| Silica Dimethyl Silate | 0.25 | 0.25 | | | |
| Silica Silylate | | | 0.25 | 0.25 | 0.5 |
| Starch | | | | 6 | 20 |
| Zinc Carbonate | | | | 2 | 3 |
| Stearyl Alcohol | 13.5 | 13.5 | 13.5 | | |
| Castor Wax | 4.5 | 4.5 | 4.5 | | |
| Behenyl Alcohol | 0.2 | 0.2 | 0.2 | | |
| C20-40 Pareth 10 | 2 | | | | |
| EDTA | | | 0.1 | 0.1 | |
| Ozokerite | 1.6 | 1.6 | 1.6 | 12 | 9 |
| Talc | 8 | 12 | 4 | 8 | |
| Magnesium Carbonate & Magnesium Hydroxide (Dead sea salt-average particle size 2 microns) | 4 | | | | 8 |
| Lupamin | | | 8 | | |
| Cyclodextrin | 4 | 4 | 4 | 4 | 4 |
| thymol | 0.05 | 0.05 | | | |
| Hexamidine | 0.1 | 0.1 | 0.1 | 0.1 | 0.1 |
| Octopirox (Piroctone Olamine) | 0.5 | 0.5 | 0.5 | 0.5 | 0.5 |
| Fragrance | 1 | | | | 2 |
|  | 100 | 100 | 100 | 100 | 100 |

F. Iron Affinity—Log $K_1$

The strength of the association between a ligand and metal, in this case iron, can be termed iron affinity. A high iron binding affinity is required for chelators to effectively compete with iron salt impurities that reduce the efficacy of 2-pyridinol-N-oxide materials.

Affinity between a metal (M) and ligand (L) can be measured by the stepwise association constant, $K_1$ which describes the following equilibrium:

$$M + L \rightleftharpoons ML; K_1 = \frac{[ML]}{[M][L]}$$

The affinity constant is conveniently expressed as the logarithm (log $K_1$) and the larger the magnitude of this number, the stronger the association between the metal (iron ions in this case) and ligand.

TABLE 5

Iron Binding Affinities of Chelators

| Chelator | Log $K_1$ [a] |
|---|---|
| Desferrioxamine | 31 |
| Diethylenetriaminepentaacetic acid (DTPA) | 28 |
| Diethylenetriaminepentakis (methylenephosphonic acid) (DTPMP) | 23 |
| Methylglycine diacetic acid (MGDA) | 16 |
| Citric Acid | 11 |

[a] NIST Standard Reference Database 46: Critically Selected Stability Constants of Metal Complexes.

In an embodiment of the present invention, the deodorant composition may contain an iron chelator which has a log $K_1$ greater than about 16. In a further embodiment, the deodorant composition may contain an iron chelator which has a log $K_1$ greater than about 20.

Antiperspirant/Deodorant Composition

The antiperspirant and/or deodorant compositions (for simplicity sometimes referred to as either antiperspirant or deodorant compositions) as described herein can contain a primary structurant, an antiperspirant active, one or more deodorant actives, a perfume, and additional chassis ingredient(s). The deodorant composition may further comprise other optional ingredient(s). The compositions can be in the form of a solid stick. The compositions can have a product hardness of about 600 gram force or more. The compositions may be free of dipropylene glycol, added water, castor wax, or any combination thereof. The deodorant composition may be anhydrous. The deodorant composition may be free of added water.

Hardness

The deodorant compositions of the present invention can have a product hardness of least about 600 gram-force, more specifically from about 600 gram-force to about 5,000 gram-force, still more specifically from about 750 gram-force to about 2,000 gram-force, and yet more specifically from about 800 gram.force to about 1,400 gram.force.

The term "product hardness" or "hardness" as used herein is a reflection of how much force is required to move a penetration cone a specified distance and at a controlled rate into an antiperspirant or deodorant composition under the test conditions described herein below. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45-degree angle penetration cone through the composition for a distance of 10 mm at a speed of 2 mm/second. The standard cone is available from Texture Technology Corp., as part number TA-15, and has a total cone length of about 24.7 mm, angled cone length of about 18.3 mm, and a maximum diameter of the angled surface of the cone of about 15.5 mm. The cone is a smooth, stainless steel construction and weighs about 17.8 grams.

Primary Structurants

The deodorant and antiperspirant compositions of the present invention comprise a suitable concentration of a primary structurant to help provide the compositions with the desired viscosity, rheology, texture and/or product hardness, or to otherwise help suspend any dispersed solids or liquids within the composition.

The term "solid structurant" as used herein means any material known or otherwise effective in providing suspending, gelling, viscosifying, solidifying, and/or thickening properties to the composition or which otherwise provide structure to the final product form. These solid structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof.

The concentration and type of solid structurant selected for use in the deodorant and antiperspirant compositions will vary depending upon the desired product hardness, rheology, and/or other related product characteristics. For most structurants suitable for use herein, the total structurant concentration ranges from about 5% to about 35%, more typically from about 10% to about 30%, or from about 7% to about 20%, by weight of the composition. In some embodiments, the structurants may be from about 20%, about 30%, about 40% to about 40%, about 50%, about 60%, or about 70%, by weight, of the composition.

Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; solid triglycerides; behenyl alcohol, or combinations thereof. The deodorant stick may further comprise one or more structural elements selected from the group consisting of waxes, natural oils, coconut oil, fractionated coconut oil, jojoba seed oil, olive oil, soybean oil, sunflower oil, any liquid triglyceride (defined as a triglyceride that is liquid at 25° C.), and combinations thereof.

Other non-limiting examples of primary structurants suitable for use herein are described in U.S. Pat. No. 5,976,514 (Guskey et al.) and U.S. Pat. No. 5,891,424 (Bretzler et al.), the descriptions of which are incorporated herein by reference.

Antiperspirant Active

The antiperspirant stick compositions of the present invention can comprise a particulate antiperspirant active suitable for application to human skin. The concentration of antiperspirant active in the composition should be sufficient to provide the desired perspiration wetness and odor control from the antiperspirant stick formulation selected.

The antiperspirant stick compositions of the present invention comprise an antiperspirant active at concentrations of from about 0.5% to about 60%, and more specifically from about 5% to about 35%, by weight of the composition. These weight percentages are calculated on an anhydrous metal salt basis exclusive of water and any complexing agents such as, for example, glycine, and glycine salts. The antiperspirant active as formulated in the composition can be in the form of dispersed particulate solids having an average particle size or equivalent diameter of less than about 100 microns, more specifically less than about 20 microns, and even more specifically less than about 10 microns.

The antiperspirant active for use in the anhydrous antiperspirant compositions of the present invention may include any compound, composition or other material having antiperspirant activity. More specifically, the antiperspirant actives may include any of the antimicrobial discussed above, or may also include astringent metallic salts, especially inorganic and organic salts of aluminum, zirconium and zinc, as well as mixtures thereof. Even more specifically, the antiperspirant actives may include aluminum-containing and/or zirconium-containing salts or materials, such as, for example, aluminum halides, aluminum chlorohydrate, aluminum hydroxyhalides, zirconyl oxyhalides, zirconyl hydroxyhalides, and mixtures thereof.

Aluminum salts for use in the anhydrous antiperspirant stick compositions include those that conform to the formula:

$$Al_2(OH)_aCl_b \cdot xH_2O,$$

wherein a is from about 2 to about 5;
the sum of a and b is about 6;
x is from about 1 to about 6; and
a, b, and x may have non-integer values.

More specifically, aluminum chlorohydroxides referred to as "5/6 basic chlorohydroxide" may be used, wherein a=5, and "2/3 basic chlorohydroxide", wherein a=4.

Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, the disclosures of which are incorporated herein by reference for the purpose of describing processes for preparing aluminum salts.

Mixtures of aluminum salts are described in British Patent Specification 1,347,950, Shin et al., published Feb. 27, 1974, which description is also incorporated herein by reference.

Zirconium salts for use in the anhydrous antiperspirant stick compositions include those which conform to the formula:

$$ZrO(OH)_{2-a}Cl_a \cdot xH_2O,$$

wherein a is from about 1.5 to about 1.87;
x is from about 1 to about 7; and
a and x may both have non-integer values.

These zirconium salts are described in Belgian Patent 825,146, Schmitz, issued Aug. 4, 1975, which description is incorporated herein by reference. Zirconium salts that additionally contain aluminum and glycine, commonly known as "ZAG complexes," are believed to be especially beneficial. These ZAG complexes contain aluminum chlorohydroxide and zirconyl hydroxy chloride conforming to the above-described formulas. Such ZAG complexes are described in U.S. Pat. No. 3,792,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, disclosures of which are incorporated herein by reference for the limited purpose of describing ZAG complexes.

Also suitable for use herein are enhanced efficacy aluminum-zirconium chlorohydrex-amino acid which typically has the empirical formula $Al_nZr(OH)_{[3n+4-m(n+1)]}(Cl)_{[m(n+1)]} \cdot AA_q$ where n is 2.0 to 10.0, preferably 3.0 to 8.0; m is about 0.48 to about 1.11 (which corresponds to M:Cl approximately equal to 2.1-0.9), preferably about 0.56 to about 0.83 (which corresponds to M:Cl approximately equal to 1.8-1.2); q is about 0.8 to about 4.0, preferably about 1.0 to 2.0; and AA is an amino acid such as glycine, alanine, valine, serine, leucine, isoleucine, β-alanine, cysteine, β-amino-n-butyric acid, or γ-amino-n-butyric acid, preferably glycine. These salts also generally have some water of hydration associated with them, typically on the order of 1 to 5 moles per mole of salt (typically, about 1% to about 16%, more typically about 4% to about 13% by weight). These salts are generally referred to as aluminum-zirconium trichlorohydrex or tetrachlorohydrex when the Al:Zr ratio is between 2 and 6 and as aluminum-zirconium pentachlorohydrex or octachlorohydrex when the Al:Zr ratio is between 6 and 10. The term "aluminum-zirconium chlorohydrex" is intended to embrace all of these forms. The preferred aluminum-zirconium salt is aluminum-zirconium chlorohydrex-glycine. Additional examples of suitable high efficacy antiperspirant actives can include Aluminum Zirconium Pentachlorohydrex Glycine, Aluminum Zirconium Octachlorohydrex Glycine, or a combination thereof. These high efficacy actives are more fully described in U.S. App. Pub. No. 2007/0003499 by Shen et al. filed Jun. 30, 2005.

Perfume

Perfumes are often a combination of many raw materials, known as perfume raw materials. Any perfume suitable for use in an antiperspirant or deodorant composition may be used herein.

Additional Chassis Ingredients

Additional Structurant

The deodorant or antiperspirant composition can further comprise an additional structurant. The additional structurant may be present in an amount from 1% to about 10%, by weight of the composition. The additional structurant(s) will likely be present at an amount less than the primary structurant.

Non-limiting examples of suitable additional structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; and solid triglycerides; behenyl alcohol, or combinations thereof.

Other non-limiting examples of additional structurants suitable for use herein are described in U.S. Pat. No. 5,976,514 (Guskey et al.) and U.S. Pat. No. 5,891,424 (Bretzler et al.).

Solvent

The antiperspirant or deodorant composition of the present invention comprises a solvent at concentrations ranging from about 20% to about 80%, and more specifically from about 30% to about 70%, by weight of the composition. The solvent can be a volatile silicone which may be cyclic or linear.

"Volatile silicone" as used herein refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976), which descriptions are incorporated herein by reference.

The volatile silicone can be a cyclic silicone having from 3 to 7, and more specifically from 5 to 6, silicon atoms, and still more specifically 5, like cyclopentasiloxane. These cyclic silicone materials will generally have viscosities of less than about 10 centistokes at 25° C.

Linear volatile silicone materials suitable for use in the antiperspirant and deodorant compositions include those represented by the formula:

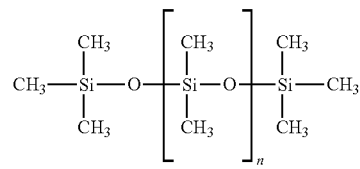

wherein n is from 1 to 7, and more specifically from 2 to 3. These linear silicone materials will generally have viscosities of less than about 5 centistokes at 25° C.

Specific examples of volatile silicone solvents suitable for use in the antiperspirant and deodorant compositions include, but are not limited to, Cyclomethicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

Non-Volatile Organic Fluids

Non-volatile organic fluids may be present, for example, in an amount of about 15% or less, by weight of the composition.

Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate, and isobutyl stearate.

Other Optional Ingredients

The anhydrous deodorant and antiperspirant compositions of the present invention may further comprise any optional material that is known for use in antiperspirant and deodorant compositions or other personal care products, or which is otherwise suitable for topical application to human skin.

One example of an optional ingredient is a scent expression material. Scent expression or release technology may be employed with some or all of the fragrance materials to define a desired scent expression prior to use and during use of the antiperspirant or deodorant products. Such scent expression or release technology can include cyclodextrin complexing material, like beta cyclodextrin. Other materials, such as, for example, starch-based matrices or microcapsules may be employed to "hold" fragrance materials prior to exposure to bodily-secretions (e.g., perspiration). The encapsulating material may have release mechanisms other than via a solvent; for example, the encapsulating material may be frangible, and as such, rupture or fracture with applied shear and/or normal forces encountered during application and while wearing. A microcapsule may be made from many materials, one example is polyacrylates.

Another example of optional materials are clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Talc, if used at higher levels can produce a significant amount of white residue which has been found to be a consumer negative for product acceptance. Therefore it is best to limit the composition to less than 10%, less than about 8%, less than about 6%, or less than about 3%, by weight of the composition.

Nonlimiting examples of other optional materials include emulsifiers, distributing agents, antimicrobials, pharmaceutical or other topical active, preservatives, surfactants, and so forth. Examples of such optional materials are described in U.S. Pat. No. 4,049,792 (Elsnau); U.S. Pat. No. 5,019,375 (Tanner et al.); and U.S. Pat. No. 5,429,816 (Hofrichter et al.); which descriptions are incorporated herein by reference.

G. Test Methods

1. Tier 1 Anaerobic MIC Assay

The data in Table 1 above was generated with the following test method. The purpose of this assay is to determine if a compound or formulation has an antimicrobial effect in vitro.

It is understood that when not specifically noted in this procedure:

a) All materials, reagents and equipment required for this procedure are of appropriate design and condition of cleanliness and/or sterility as determined by their intended use.

b) The operator has been trained in aseptic technique and has been qualified to perform the procedure and accurately interpret the results.

c) All media required for this procedure was manufactured by a reputable commercial source eg. Difco, Merck etc. and has been stored and prepared as per manufacturer's instructions.

d) All routine laboratory controls, including but not limited to, media function and growth promotion tests, verification of sterility and use of positive and negative controls are being conducted.

Procedure: (all Procedures Performed in Anaerobic Chamber Except where Noted)

1. Apparatus

Incubator at 37° C.; 20-200 ul 12 channel pipette; 5-50 ul 12 channel pipette; 1250 ul 8 channel Thermo Scientific Matrix pipette; 96 well plate shaker (located in incubator); Beckman Coulter deep well cap mat #267005; Beckman Coulter deep 96 well plates #267007; Falcon 96 well tissue culture plates #353072; Vortexer; Culture tubes/caps Disposable sterile gloves; Sterile petri dishes; Standard microbiological lab equipment (sterile pipettes, syringes, tips, loops, etc.); Glass bottles/flasks for media; Autoclave; Parafilm; Spectrophotometer.

2. Media 0.9% or 0.85% saline solution
BHI agar supplemented with 1% Tween 80
BHI media supplemented with 1% Tween 80

3. Microbial Strains

*Staphylococcus epidermidis* (clinical isolate)
*Corynebacterium mucofaciens* (clinical isolate)

4. Test Procedure

Inoculum Preparation

Prior to testing streak organisms for isolation on BHI with 1% Tween 80 plates, wrap with parafilm and place in 37° C. incubator. When isolated colonies appear remove one representative colony from each plate and place each in 5 ml of BHI with 1% Tween 80 media. Incubate at 37° C. with shaking overnight. Inoculate 20 ml BHI with 1% Tween 80 (per 96 deep well plate to be tested) with 20 ul of the overnight culture (1-1000 dilution).

Master Plate Preparation

Compounds/formulations to be tested are diluted across a 96 deep well plate as shown below (for a 1% stock solution). 800 ul of 0.85% saline is added to wells A1 and B1 (as these will be the negative and positive control respectively). 800 ul each 1% stock solution+ positive control are added to wells C1 through H1. 400 ul 0.85% saline are added to all other wells. 400 ul is then removed from #1 well added to the #2 well and mixed. This is then continued across the plate resulting in a 50% dilution between wells across the plate (this can be easily accomplished with an automatic 8 channel Matrix pipette set to withdraw, dispense and mix).

numerical range given throughout this specification will include every narrower numerical range that falls within such broader numerical range, as if such narrower numerical ranges were all expressly written herein.

H. Additional Examples/Combinations

A. A deodorant stick comprising:
a) from about 0.1% to about 10% of a substituted or unsubstituted 2-pyridinol-N-oxide material;

|   | 1 | 2 | 3 | 4 | 5 | 6 | 7 | 8 | 9 | 10 | 11 | 12 |
|---|---|---|---|---|---|---|---|---|---|----|----|----|
| A | 800 ul saline | 400 ul NaCl | 400 ul 1 NaC | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl |
| B | 800 ul saline | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl |
| C | 800 + control | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl |
| D | 800 ul compond 1 | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl |
| E | 800 ul compond 2 | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl |
| F | 800 ul compond 3 | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl |
| G | 800 ul compond 4 | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl |
| H | 800 ul compond 5 | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl | 400 ul NaCl |

|   | 1 | 2 | 3 | 4 | 5 | 6 | 7 | 8 | 9 | 10 | 11 | 12 |
|---|---|---|---|---|---|---|---|---|---|----|----|----|
| A | Media Blank | Media Blank | Media Blank | Media Blank | Media Blank | Media Blank | Media Blank | Media Blank | Media Blank | Media Blank | Media Blank | Media Blank |
| B | POS | POS | POS | POS | POS | POS | POS | POS | POS | POS | POS | POS |
| C | 0.1 | 0.05 | 0.025 | 0.0125 | 0.00625 | 0.003125 | 0.0015625 | 0.00078125 | 0.000390625 | 0.000195313 | 9.76563E−05 | 4.88281E−05 |
| D | 0.1 | 0.05 | 0.025 | 0.0125 | 0.00625 | 0.003125 | 0.0015625 | 0.00078125 | 0.000390625 | 0.000195313 | 9.76563E−05 | 4.88281E−05 |
| E | 0.1 | 0.05 | 0.025 | 0.0125 | 0.00625 | 0.003125 | 0.0015625 | 0.00078125 | 0.000390625 | 0.000195313 | 9.76563E−05 | 4.88281E−05 |
| F | 0.1 | 0.05 | 0.025 | 0.0125 | 0.00625 | 0.003125 | 0.0015625 | 0.00078125 | 0.000390625 | 0.000195313 | 9.76563E−05 | 4.88281E−05 |
| G | 0.1 | 0.05 | 0.025 | 0.0125 | 0.00625 | 0.003125 | 0.0015625 | 0.00078125 | 0.000390625 | 0.000195313 | 9.76563E−05 | 4.88281E−05 |
| H | 0.1 | 0.05 | 0.025 | 0.0125 | 0.00625 | 0.003125 | 0.0015625 | 0.00078125 | 0.000390625 | 0.000195313 | 9.76563E−05 | 4.88281E−05 |

Test Plate Preparation

In row A of a 96 deep well plate pipette 180 ul of sterile BHI with 1% Tween 80 as a negative growth control. All other wells receive 180 ul of inoculum. From the master plate introduce 20 ul to the corresponding row in the test plate using an 8-channel pipette. Loaded plates are placed on a plate shaker in the 37° C. incubator and incubated overnight. The next day read the O.D. 600 on a plate reader. The MIC is the last well from the right that has no bacterial growth.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every b) from about 0.01% to about 15% of an iron chelator selected from the group consisting of:
(1) Iron chelators represented by the following structure:

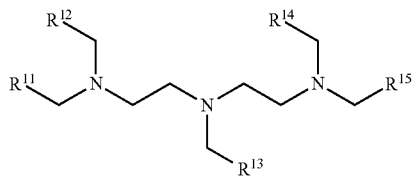

where $R^{10}$, $R^{11}$, $R^{12}$, $R^{13}$, $R^{14}$ are selected from the group consisting of $M^1M^2PO_3$, $CO_2M^1$, and mixtures thereof where $M^1$ and $M^2$ are independently selected from the group consisting of H, a metal salt and an ammonium salt;

(2) Iron chelators represented by the following structure:

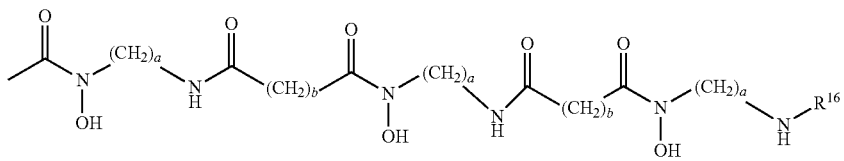

where a is an integer from 2 to 7 wherein any of the $CH_2$ groups in this unit may be substituted with alkyl or aryl units that may contain heteroatoms (S, N, O, Cl, Fe, Br or I)

where b is an integer from 1 to 7 wherein any of the $CH_2$ groups in this unit may be substituted with alkyl or aryl units that may contain heteroatoms (S, N, O, Cl, Fe, Br or I)

where $R^{16}$ is H or $(CH_2)_n$, where n in an integer from 1 to 6 or is a $CH_2$ linker unit that may be further substituted at any $CH_2$ group in the chain with alkyl or aryl units that may contain heteroatoms (S, N, O, Cl, F, Br, or I).

B. The deodorant stick according to Paragraph A, wherein the iron chelator has a log $K_1$ greater than about 16.

C. The deodorant stick according to Paragraph A-B, wherein the iron chelator has a log $K_1$ greater than about 20.

D. The deodorant stick according to Paragraph A-C, where the substituted or unsubstituted 2-pyridinol-N-oxide material comprises the molecular structure:

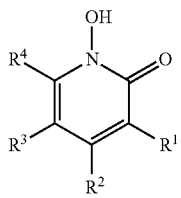

wherein $R^1$, $R^2$, $R^3$, $R^4$ are independently selected from the group consisting of H, Cl, Br, I, F, NO, $NO_2$, $(CH_2)_nG$, and mixtures thereof, wherein each G is independently selected from the group consisting of $(O)_mSO_3M^3$, $(O)_mCO_2M^3$, $(O)_mC(O)(R^5)$, $(O)_mC(O)N(R^5R^6)$, $(O)_mCN$, $(O)_m(R^5)$, $N(R^5R^6)$, and mixtures thereof, wherein m is 0 or 1, and wherein n is an integer from 0 to 4, and wherein $R^5$ and $R^6$ are independently selected from the group consisting of H and a substituted or unsubstituted C1-C12 organic group, and wherein $M^3$ is selected from the group consisting of H, a substituted or unsubstituted $C_1$-$C_{12}$ organic group, $+N(R^7R^8R^9R^{10})$, and 1/q M' q+ wherein M' is selected from the group consisting of an alkali metal of charge q and an alkaline earth metal of charge q, where R7, R8, R9, and R10 are independently selected from the group consisting of H and a substituted or unsubstituted $C_1$-$C_{12}$ organic group, and wherein any pair of vicinal groups, $R^1$ and $R^2$, $R^2$ and $R^3$, $R^3$ and $R^4$, may be taken together to form another five- or six-membered aromatic or aliphatic ring optionally substituted with one or more groups selected from the group consisting of Cl, Br, I, F, NO, $NO_2$, CN, $(CH_2)_nG$, and mixtures thereof.

E. The deodorant stick according to Paragraph A-D, wherein $R^1$, $R^2$, $R^3$, $R^4$ are selected from the group consisting of H, Cl, and $(CH_2)_nG$, wherein G is selected from the group consisting of $(O)_mSO_3M^3$, $(O)_mCO_2M^3$, $(O)_mC(O)(R^5)$, $(O)_mCN$, and $(O)_m(R^5)$, wherein m is 0 or 1.

F. The deodorant stick according to Paragraph A-E, wherein said substituted or unsubstituted 2-pyridinol-N-oxide material is 1-hydroxy-4-methyl-6-(2,4,4-trimethylpentyl)-2-pyridone monoethanolamine salt.

G. The deodorant stick according to Paragraph A-F, wherein the iron chelator is diethylenetriaminepentaacetic acid (DTPA).

H. The deodorant stick according to Paragraph A-G, wherein the iron chelator is Diethylenetriaminepentakis (methylenephosphonic acid) (DTPMP).

I. The deodorant stick according to Paragraph A-H, wherein the iron chelator is Desferrioxamine.

J. The deodorant stick according to Paragraph A-I, wherein the substituted or unsubstituted 2-pyridinol N-oxide material is from about 0.3% to about 3%.

K. The deodorant stick according to Paragraph A-J, the substituted or unsubstituted 2-pyridinol N-oxide material is from about 0.5% to about 2%.

L. The deodorant stick according to Paragraph A-K, wherein the iron chelator is from about 0.3% to about 6%.

M. The deodorant stick according to Paragraph A-L, wherein the iron chelator is from about 0.5% to about 4%.

N) Use of the deodorant stick according to Paragraph A-M, for treating underarm skin.

O) Use of the deodorant stick according to Paragraph A-M, for boosting the anti-bacterial performance.

P) Use according to Paragraph 0, for treating cosmetically underarm skin against C. mucofaciens and/or S. epidermidis Q) Use according to Paragraph O or P, wherein the deodorant stick comprises from 0.1% to 10%, preferably from 0.3% to 3%, more preferably from 0.5% to 2% of 1-hydroxy-4-methyl-6-(2,4,4-trimethylpentyl)-2-pyridone monoethanolamine salt and from 0.01% to 15%, preferably from 0.3% to 6%, more preferably from 0.5% to 4% of an iron chelator which is selected from the group consisting of diethylenetriaminepentaacetic acid (DTPA), Diethylenetriaminepentakis (methylenephosphonic acid) (DTPMP), Desferrioxamine, and mixtures thereof.

R) The personal care composition according to Paragraph A-M for use in a method of treating bacterial agents onto underarm skin.

S) The personal care composition according to Paragraph A-M, for use in a method of inhibiting the growth *C. mucofaciens* and/or *S. epidermidis* onto underarm skin.

The devices, apparatuses, methods, components, and/or compositions of the present invention can include, consist essentially of, or consist of, the components of the present invention as well as other ingredients described herein. As used herein, "consisting essentially of" means that the devices, apparatuses, methods, components, and/or compositions may include additional ingredients, but only if the additional ingredients do not materially alter the basic and novel characteristics of the claimed devices, apparatuses, methods, components, and/or compositions.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A deodorant stick comprising:
   a. a substituted or unsubstituted 2-pyridinol-N-oxide material; and
   b. a chelant, wherein the ratio of chelant to the substituted or unsubstituted 2-pyridinol-N-oxide material is at least about 4:1.

2. The deodorant stick of claim 1, further comprising at least one antimicrobial material selected from the group consisting of hexamidine, magnesium carbonate, zinc carbonate, thymol, magnesium hydroxide, dead sea salt, magnesium hydroxide and magnesium carbonate hydroxide, partially carbonated magnesium hydroxide, magnesium carbonate hydroxide, calcium carbonate, polyvinyl formate, salycilic acid, niacinamide, cinnamon essential oil, cinnamon bark essential oil, cinnamic aldehyde, and combinations thereof.

3. The deodorant stick of claim 1, wherein the chelant is an iron chelator selected from the group consisting of:

i. Iron chelators represented by the following structure:

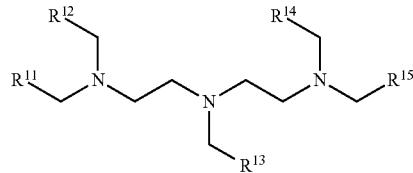

where $R^{10}$, $R^{11}$, $R^{12}$, $R^{13}$, $R^{14}$ are selected from the group consisting of $M^1M^2PO_3$, $CO_2M^1$, and mixtures thereof where $M^1$ and $M^2$ are independently selected from the group consisting of H, a metal salt and an ammonium salt;

ii. Iron chelators represented by the following structure:

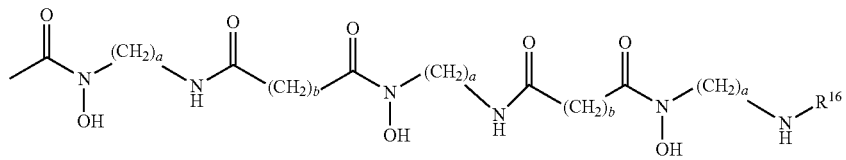

where a is an integer from 2 to 7 wherein any of the $CH_2$ groups in this unit may be substituted with alkyl or aryl units that may contain heteroatoms (S, N, O, Cl, Fe, Br or I)

where b is an integer from 1 to 7 wherein any of the $CH_2$ groups in this unit may be substituted with alkyl or aryl units that may contain heteroatoms (S, N, O, Cl, Fe, Br or I)

where $R^{16}$ is H or $(CH_2)_n$, where n in an integer from 1 to 6 or is a $CH_2$ linker unit that may be further substituted at any $CH_2$ group in the chain with alkyl or aryl units that may contain heteroatoms (S, N, O, Cl, F, Br, or I).

4. The deodorant stick of claim 1, wherein the chelant is selected from the group consisting of diethylenetriaminepentaacetic acid (DTPA), diethylenetriaminepentakis (methylenephosphonic acid) (DTPMP), desferrioxamine, EDTA, DPTA, and combinations thereof.

5. The deodorant stick claim 1, wherein the deodorant stick comprises from about 0.1% to about 10% by weight of substituted or unsubstituted 2-pyridinol-N-oxide material.

6. The deodorant stick of claim 1, wherein the deodorant stick comprises from about 0.01% to about 15% by weight of the chelant.

7. The deodorant stick of claim 1, wherein the deodorant stick is substantially anhydrous.

8. The deodorant stick of claim 1, wherein the deodorant stick further comprises one or more structural elements selected from the group consisting of waxes, natural oils, coconut oil, fractionated coconut oil, jojoba seed oil, olive oil, soybean oil, sunflower oil, liquid triglycerides, and combinations thereof.

9. The deodorant stick of claim 2, wherein the substituted or unsubstituted 2-pyridinol-N-oxide material and the antimicrobial material each have a raw material microbial inhibition concentration of at most about 2500 ppm.

10. A deodorant stick comprising:
    a. substituted or unsubstituted 2-pyridinol-N-oxide material; and
    b. from about 0.01% to about 15% by weight a chelant;
       wherein the deodorant stick is substantially anhydrous.

11. The deodorant stick of claim 10, wherein the chelant is an iron chelant selected from the group consisting of:

iii. Iron chelators represented by the following structure:

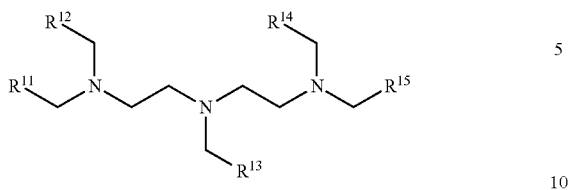

where $R^{10}, R^{11}, R^{12}, R^{13}, R^{14}$ are selected from the group consisting of $M^1M^2PO_3$, $CO_2M^1$, and mixtures thereof where $M^1$ and $M^2$ are independently selected from the group consisting of H, a metal salt and an ammonium salt;

iv. Iron chelators represented by the following structure:

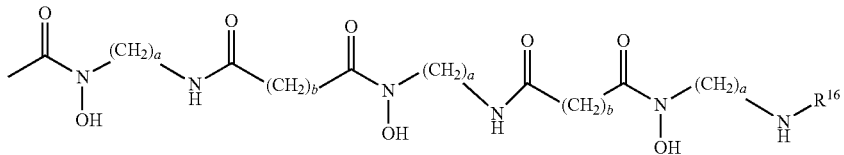

where a is an integer from 2 to 7 wherein any of the $CH_2$ groups in this unit may be substituted with alkyl or aryl units that may contain heteroatoms (S, N, O, Cl, Fe, Br or I)

where b is an integer from 1 to 7 wherein any of the $CH_2$ groups in this unit may be substituted with alkyl or aryl units that may contain heteroatoms (S, N, O, Cl, Fe, Br or I)

where $R^{16}$ is H or $(CH_2)_n$, where n in an integer from 1 to 6 or is a $CH_2$ linker unit that may be further substituted at any $CH_2$ group in the chain with alkyl or aryl units that may contain heteroatoms (S, N, O, Cl, F, Br, or I).

12. The deodorant stick of claim 10, wherein the chelant is selected from the group consisting of diethylenetriaminepentaacetic acid (DTPA), diethylenetriaminepentakis (methylenephosphonic acid) (DTPMP), desferrioxamine, EDTA, DPTA, and combinations thereof.

13. The deodorant stick of claim 10, wherein the deodorant stick further comprises at least one of the group consisting of hexamidine, magnesium carbonate, zinc carbonate, thymol, magnesium hydroxide, dead sea salt, magnesium hydroxide and magnesium carbonate hydroxide, partially carbonated magnesium hydroxide, magnesium carbonate hydroxide, calcium carbonate, polyvinyl formate, salycilic acid, niacinamide, cinnamon essential oil, cinnamon bark essential oil, cinnamic aldehyde, and combinations thereof.

14. The deodorant stick of claim 10, wherein the deodorant stick further comprises one or more structural elements selected from the group consisting of waxes, natural oils, coconut oil, fractionated coconut oil, jojoba seed oil, olive oil, soybean oil, sunflower oil, liquid triglycerides, and combinations thereof.

15. The deodorant stick of claim 10, wherein the piroctone olamine and chelant each have a microbial inhibition concentration of at most about 2500 ppm.

* * * * *